United States Patent [19]

Miura et al.

[11] Patent Number: 4,905,499

[45] Date of Patent: Mar. 6, 1990

[54] DEVICE FOR DETECTING VISCOSITY OR SPECIFIC GRAVITY OF LIQUID

[75] Inventors: Shinsuke Miura; Susumu Ishizuka, both of Tokyo, Japan

[73] Assignee: Yamaichi Electric Mfg. Co., Ltd., Tokyo, Japan

[21] Appl. No.: 179,216

[22] Filed: Apr. 8, 1988

[30] Foreign Application Priority Data

Apr. 30, 1987 [JP] Japan .................. 62-107389

[51] Int. Cl.[4] .................. G01N 9/24; G01N 11/10
[52] U.S. Cl. .................. 73/32 A; 73/54
[58] Field of Search .................. 73/54, 59, 32 A, 430

[56] References Cited

U.S. PATENT DOCUMENTS

| | | | |
|---|---|---|---|
| 3,903,732 | 9/1975 | Rork et al. | 73/54 |
| 4,217,774 | 8/1980 | Agar | 73/32 A |
| 4,240,285 | 12/1980 | Langdon | 73/32 A |

Primary Examiner—Hezron E. Williams
Assistant Examiner—Joseph W. Roskos
Attorney, Agent, or Firm—Wenderoth, Lind & Ponack

[57] ABSTRACT

A device for detecting the viscosity or specific gravity of liquid includes a vibrator made of piezoelectric ceramics and capable of vibrating about its axis, a vibration transmission member, a detection terminal to be immersed in liquid, the viscosity or specific gravity of which is to be measured, and a vibration sensor provided on the vibration transmission member. The vibrator and detection terminal are connected to each other through the vibration transmission member. The detection terminal is vibrated within the liquid by the vibration of the vibrator transmitted through the vibration transmission member. The vibration sensor detects the vibration of the detection terminal immersed in the liquid.

4 Claims, 7 Drawing Sheets

DEVICE FOR DETECTING VISCOSITY OR SPECIFIC GRAVITY OF LIQUID

BACKGROUND OF THE INVENTION AND RELATED ART STATEMENT

The present invention relates to a device for detecting the viscosity of specific gravity of liquid using a vibrator comprising piezoelectric ceramics as a drive source.

The inventors have proposed a vibrator made of piezoelectric ceramics that converts mechanical energy to electrical energy as disclosed in Japanese Patent Application No. 61-299598. The related art vibrator vibrates about an axis thereof. When the vibrator is a parallelepiped, for example, adjacent corners of the vibrator vibrate in opposite directions and each of the corners repeatedly vibrate in alternate directions parallel to the thickness of the vibrator. They have considered the applicability of this vibrator to a device for detecting the viscosity or specific gravity of liquid and have conducted experiments in which the vibrator was connected to a detection terminal for the purpose of vibrating the detection terminal both in air and in liquid and converting the difference in vibration of the detection terminal when in the air and in the liquid into an equivalent electric signal through its own conversion function. In other words, the vibrator has been used both as a drive source for the detection terminal and as a sensor for sensing a variation in the vibration of the detection terminal and converting the variation into an equivalent electric signal.

The vibrator serving as the aforementioned drive source is vibrated about its axis at a resonance frequency of a vibration system including itself and the detection terminal. When detecting the viscosity of liquid, a variation in voltage level at the time of resonance within the liquid is detected as electric signal indicative of the viscosity. When detecting the specific gravity of liquid, the variation in resonance frequency of the detection terminal within the liquid is detected as an equivalent electric signal indicative of the specific gravity.

With the application of the vibrator serving both as a drive source and as a sensor to a device for detecting the viscosity or specific gravity of liquid, it is possible to obtain measurement with some degree precision. However, the device is subject to unstable operation resulting from disturbance of the resonance point and detection errors resulting from environmental conditions, such as temperature, which produce a fluctuation in the output of a bridge circuit through which the aforementioned vibrator and a condenser are connected to each other.

SUMMARY OF THE INVENTION

The main object of the present invention is to provide a device capable of stably detecting the viscosity or specific gravity of liquid with a high degree of precision.

To achieve the object described above, according to the present invention, there is provided a device for detecting the viscosity or specific gravity of liquid, comprising a vibrator made of piezoelectric ceramics and capable of vibrating about its axis, a vibration transmission member having one end thereof connected to the vibrator, a detection terminal connected to the other end of the vibration transmission member and immersed within liquid, the viscosity or specific gravity of which is to be measured, the detection terminal being vibrated within the liquid by the vibration of the vibrator transmitted through the vibration transmission member, and a vibration sensor provided on the vibration transmission member for detecting the vibration of the detection terminal immersed in the liquid.

The above and other objects, characteristic features and advantages of the present invention will become apparent to those skilled in the art as disclosure is made in the following description of a preferred embodiment of the invention, as illustrated in the accompanying drawings.

DETAILED DESCRIPTION OF THE PREFERRED EMBODIMENT

Figure 1:
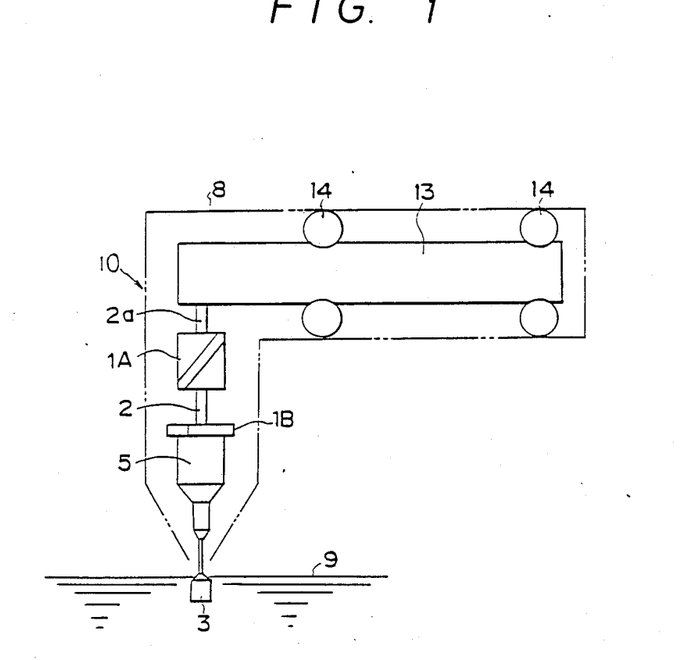
FIG. 1 is a side view schematically illustrating a detection structure of one embodiment of the device for detecting the viscosity of specific gravity of liquid according to the present invention.

The present invention will now be described in detail with reference to the illustrated embodiment. FIG. 1 is a side view illustrating the fundamental structure of one embodiment of the device for detecting the viscosity or specific gravity of liquid according to the present invention. The structure comprises a vibrator 1A vibratable about a common axis and serving as a drive source, a vibration transmission member 2 connected at one end thereof coaxially to one end of the vibrator 1A, a detection terminal 3 connected coaxially to the other end of the transmission member 2 so that the detection terminal 3 can be vibrated about the common axis by the vibration of the vibrator 1A transmitted through the transmission member, and a vibration sensor 1B integrally fitted about the transmission member 2 at a predetermined position located between the vibrator 1A and the detection terminal 3. The structure (a vibration system) may further include a mass 5 having a constant moment of inertia, which is coaxially fitted about the transmission member 2 so that the resonance frequency of the vibrator 1A can be established by the mass 5 selected.

The vibration transmission member 2 is a column or square pillar and serves not only as a carrier for supporting the detection terminal 3 at a location spaced from the vibrator 1A but also as a vibration transmitting medium. The vibration sensor 1B is made of an element capable of converting mechanical energy to electrical energy, such as piezoelectric ceramics, and detects mechanical vibration of the detection terminal 3 immersed in liquid 9 the viscosity or specific gravity of which is to be measured, via the transmission member 2 and converts the mechanical vibration into an electrical signal. The detection terminal 3 is a hollow or solid column having a circular cross section and has a circumferential surface that has a comparatively large surface area and is subjected to specular surface finishing. The detection terminal 3 may be a thin plate when it is used for detecting the specific gravity of liquid or a disk when it is used for detecting the viscosity of liquid.

With the vibration system having the aforementioned structure, the vibration of the vibrator 1A about its axis is transmitted through the transmission member 2 to the detection terminal 3 immersed in the liquid 9. As a result, the detection terminal 3 is vibrated within the liquid 9 about the common axis of the vibrator 1A, transmission member 2 and itself. When the detection terminal 3 vibrates about the common axis within the liquid 9, the detection terminal 3 is subjected to the moment of inertia of the liquid 9 to inhibit rotation of the detection terminal 3. The resistive offered against rotation varies the resonance frequency of the vibration system, and an electric signal corresponding to the variation in resonance frequency is obtained from the vibration sensor 1B.

The detection terminal 3 vibrated about the common axis within the liquid 9 does not generate wave motion which is a disturbance factor when a conventional vibrator vibrating in the vertical direction has been used, maintains the liquid 9 in a static state and, when detecting the specific gravity of the liquid 9, is subjected only to the inertial resistance offered by the liquid. When the detection terminal 3 is immersed in the liquid 9, the resonance frequency is varied to produce a deviation in the resonance point. The specific gravity of the liquid 9 is measured based on the variation in resonance frequency from the resonance point by utilizing the effect of the conversion of mechanical energy to electrical energy by piezoelectric ceramics constituting the vibration sensor 1B. When detecting the viscosity of the liquid 9, the detection terminal 3 can be subjected to only the viscous resistance offered by the liquid 9 along its circumferential surface. As a result, the resonance frequency of the vibration system is varied and the vibration sensor 1B is driven at the varied resonance frequency. The mechanical impedance of the vibration system obtained when the vibration sensor 1B has been driven at the resonance frequency corresponding to the viscous resistance imparted to the detection terminal 3 is varied to produce a variation in vibration level (voltage level) of the vibration sensor 1B. The viscosity of the liquid 9 is measured from the variation in vibration level while utilizing the aforementioned energy conversion effect.

Figure 2:
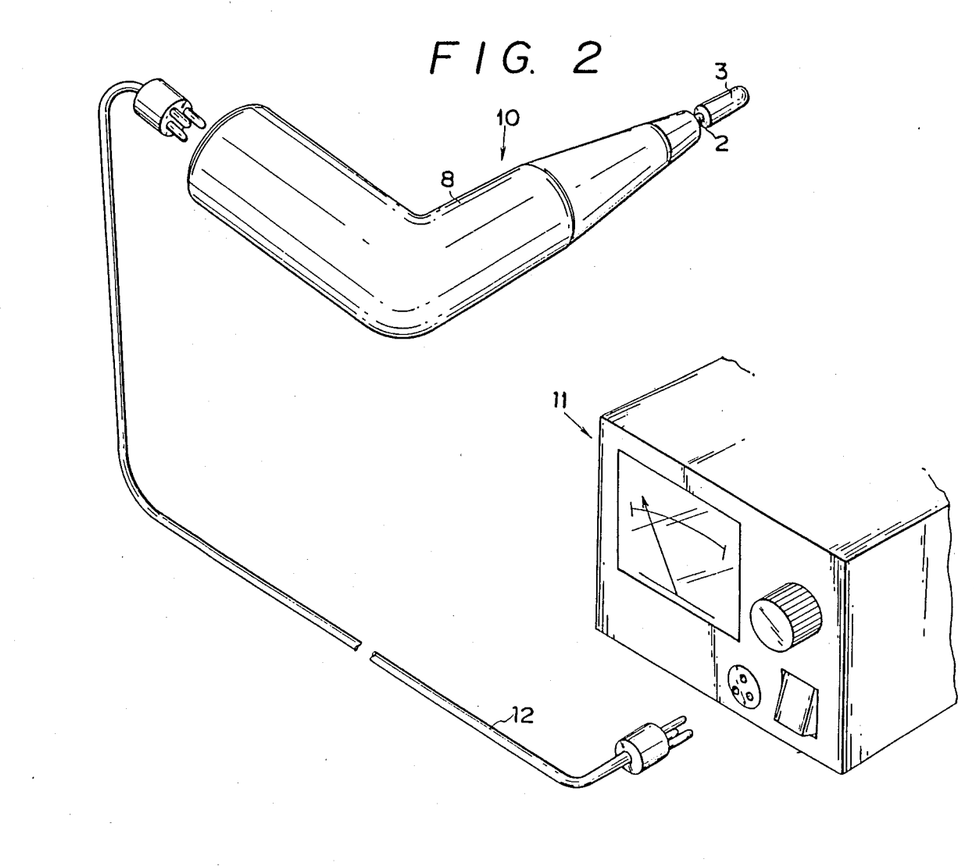
FIG. 2 is a perspective view of the device.
Figure 3:
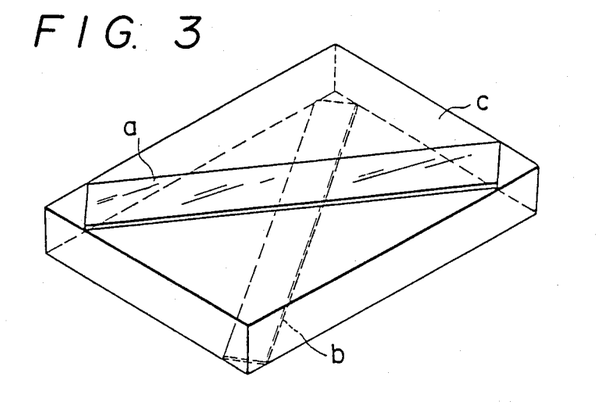
FIG. 3 is a perspective view of a vibrator used in the device.
Figure 4:
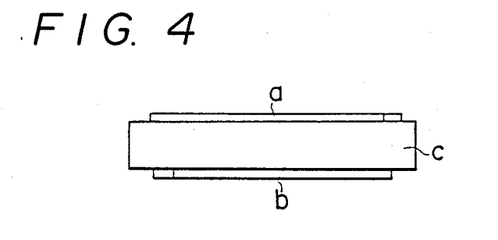
FIG. 4 is a side view of the vibrator.
Figure 5:
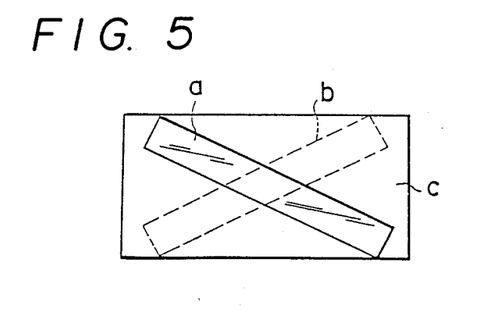
FIG. 5 is a plan view of the vibrator.

As illustrated in FIG. 2, part of the transmission member 2 and the entire detection terminal 3 are exposed, whereas the remaining part of the transmission member 2, the entire vibrator 1A and the entire vibration sensor 1B are accommodated within a handgrip type housing 8. The exposed detection terminal 3 is immersed in the liquid 9 as illustrated in FIG. 1. Furthermore, as shown in FIG. 2, a detection section 10 is connected via a connector cable 12 to a measuring device having built-in circuit means.

The vibrator 1A used as a drive source will be described in detail with reference to FIGS. 3 to 7. The vibrator 1A comprises a vibration plate c having a rectangular cross section and a pair of elongated piezoelectric ceramic members a and b attached respectively to the opposite surfaces of the vibration plate c so that they extend along the diagonals of the plate but are skewed. Each of the piezoelectric ceramic members a and b is prepared by subjecting ferroelectric ceramics to polarization treatment (poling) to impart a polarization direction to the ferroelectric ceramics. The piezoelectric ceramic member a or b elongates when a positive voltage is applied thereto and contracts when negative voltage is applied thereto, and vice versa. Thus, each of the piezoelectric ceramic members a and b vibrates in its lengthwise direction. With the aforementioned arrangement of the vibration plate c and two piezoelectric ceramic members a and b which constitute the vibrator 1A having a function of converting mechanical energy to electrical energy, when the two skewed piezoelectric ceramic members a and b having the the vibration plate c disposed therebetween are vibrated in the lengthwise direction so that they contract or elongate at the same time, the vibration plate c is vibrated in a twisting manner which will be described later in more detail.

Figure 6A:
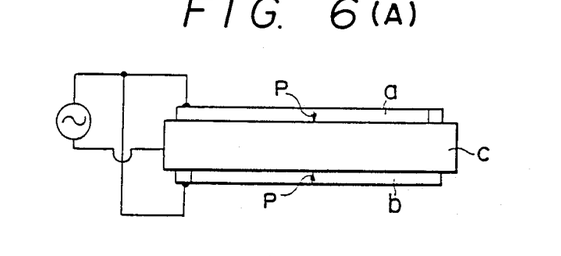
FIG. 6(A) is a schematic diagram illustrating one example of an electric connection of the vibrator.
Figure 6B:
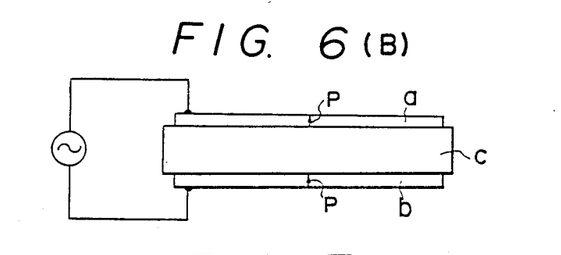
FIG. 6(B) is a schematic diagram illustrating another example of an electric connection of the vibrator.

In a parallel circuit, as shown in FIG. 6(A), the two piezoelectric ceramic members a and b are attached to the opposite surfaces of the vibration plate c so that their polarization directions p are reverse to each other. In a series circuit, as shown in FIG. 6(B), the two piezoelectric ceramic members a and b are attached to the opposite surfaces of the vibration plate c so that their polarization directions p are the same. In either of the circuits, the two piezoelectric ceramic members a and b are skew with the vibration plate c interposed therebetween.

In the illustrated embodiment, each of the piezoelectric ceramic members a and b has a single layer. This is by no means limitative. For example, a multilayer bimorph cell making the most piezoelectric ceramic characteristics may be used instead.

Figure 7:
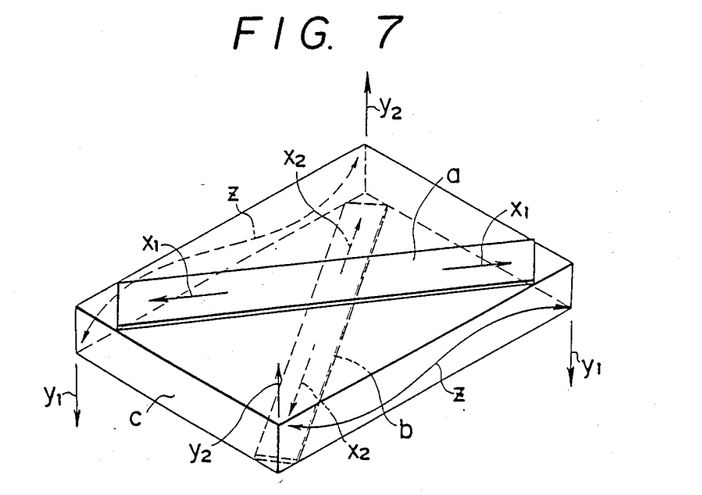
FIG. 7 is a perspective view illustrating the twisting vibration of the vibrator.

The twisting vibration of the vibration plate c will be described with reference to FIG. 7. When the piezoelectric ceramic member a elongates in the direction indicated by arrows $x_1$ and, at the same time, the piezoelectric ceramic member b elongates in the direction indicated by arrows $x_2$, one pair of diagonal portions of the vibration place c are bent in the direction indicated by arrows $y_1$ and the other pair of diagonal portions thereof are bent in the direction indicated by arrows $y_2$. Conversely, when the piezoelectric ceramic member a contracts and, at the same time, the piezoelectric ceramic member b contracts, one pair of diagonal portions of the vibration plate c are bent in the direction indicated by arrows $y_2$ and the other pair of diagonal portions are bent in the direction indicated by arrows $y_1$. In other words, the adjacent corners of the vibration plate c are bent in the opposite directions to effect twisting vibration z (multi-bending vibration) of the vibration plate c.

Returning to FIG. 1, the other end of the vibrator 1A is fixed via a shaft 2a coaxial with the transmission member 2 to a laterally extending rod-like inertia mass 13 which is tightly fixed to the inner wall of the housing 8 by means of vibration absorbing members 14, whereby transmission of the vibration to the inertia mass 13 is effected stably. It goes without saying that the inertia mass 13 may be placed vertically relative to the vibrator 1A. The vibrator 1A fixed at one end thereof to the shaft 2a vibrates about the axis of the transmission member 2 at the other end thereof, thereby transmitting vibration to the detection terminal 3 through the transmission member 2. As a result, the detection terminal 3 is vibrated about the central axis of of the transmission member 2. Therefore, the vibration of the detection terminal 3 in the liquid 9 is sensed by the vibration sensor 1B. Consequently, the vibration sensor 1B converts the variation in vibration into an equivalent electric signal to detect the specific gravity or viscosity of the liquid 9.

Now, the vibration sensor 1B will be described in detail with reference to FIGS. 8 and 10. As the vibration sensor 1B, an acceleration sensor is used, preferably an angular acceleration sensor, comprising a pair of axially symmetrical piezoelectric bimorph type vibration elements $S_1$ and $S_2$. Each of the vibration elements $S_1$ and $S_2$ may be either a combination of piezoelectric ceramic members or a combination comprising a piezoelectric ceramic member and a vibration plate (a metallic plate).

The vibration elements $S_1$ and $S_2$ are axially symmetrically attached to the vibration transmission member 2 at predetermined positions so that when the vibration about the transmission member 2 is applied to the vibration elements $S_2$ and $S_2$, the elements produce and output voltages of the same phase.

Figure 10A:
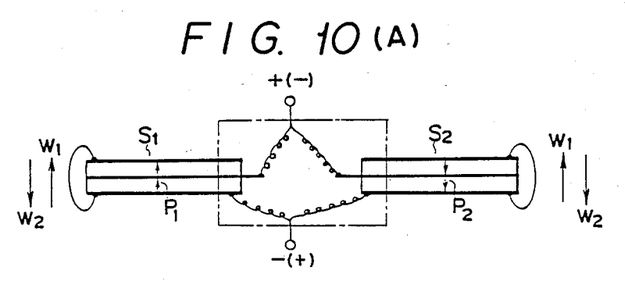
FIG. 10(A) is a schematic diagram illustrating one example of an electric connection of the vibration sensor.

In a parallel circuit, as shown in FIG. 10(A), the two layers of the vibration element $S_1$ have the same polarization direction $P_1$ and those of the vibration element $S_2$ have the same polarization direction $P_2$. The vibration elements $S_1$ and $S_2$ are attached to the transmission member 2 so that the polarization directions $P_1$ and $P_2$ are opposite to each other, and their respective internal electrodes are connected to each other and their respective external electrodes are also connected to each other so that one of the connection ends functions as a positive voltage terminal (+) and the other of the connection ends functions as a negative voltage terminal (−). With this arrangement, when the free ends of the vibration elements $S_1$ and $S_2$ are vibrated in the direction indicated by arrow $W_1$ or $W_2$ in the direction of thickness of the vibration elements $S_1$ and $S_2$, positive voltage is produced on the internal electrode of one of the vibration elements $S_1$ and $S_2$ and negative voltage on the internal electrode of the other of the vibration elements and, as a result, the positive voltage and the negative voltage offset each other. Similarly, positive voltage is produced on the external electrodes of one of the the vibration elements and negative voltage on the external electrodes of the other of the vibration elements and, as a result, the positive voltage and the negative voltage offset each other. Therefore, no voltage is output between the positive voltage terminal (+) and the negative voltage terminal (−). This indicates that no output is produced when the free ends of the vibration elements $S_1$ and $S_2$ are vibrated in the same direction.

On the other hand, when vibration about the vibration transmission member 2 is transmitted to the vibration elements $S_1$ and $S_2$ through the transmission member 2, the free end of one of the vibration elements $S_1$ and $S_2$ is vibrated in the direction indicated by the arrow $W_1$ while the free end of the other of the vibration elements is vibrated in the opposite direction indicated by the arrow $W_2$, resulting in positive (or negative) voltages of the same phase being produced on the internal electrodes and negative (or positive) voltages of the same phase being produced on the external electrodes and, consequently, output is produced between the positive voltage terminal (+) and the negative voltage terminal (−).

Figure 10B:
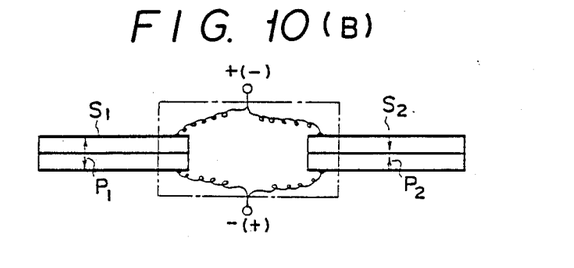
FIG. 10(B) is a schematic diagram illustrating another example of an electric connection of the vibration sensor.

In a series circuit, as shown in FIG. 10(B), the two layers of one of the vibration elements $S_1$ and $S_2$ have two polarization directions which are directed toward each other and those of the other of the vibration elements have two polarization directions which are directed away from each other. One of external electrodes of the vibration element $S_1$ is connected to one of the external electrodes of the vibration element $S_2$ and the other of the external electrodes of the vibration element $S_1$ is also connected to the other of the external electrodes of the vibration element $S_2$ so that one of the connection ends functions as a positive voltage terminal (+) and the other of the connection ends functions as a negative voltage terminal (−). In this embodiment, the vibration elements $S_1$ and $S_2$ are actuated in the same manner as in the embodiment shown in FIG. 10(A).

Figure 8:
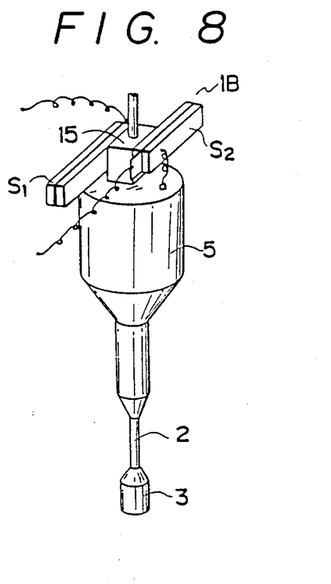
FIG. 8 is a perspective view of a vibration sensor used in the device.
Figure 9:
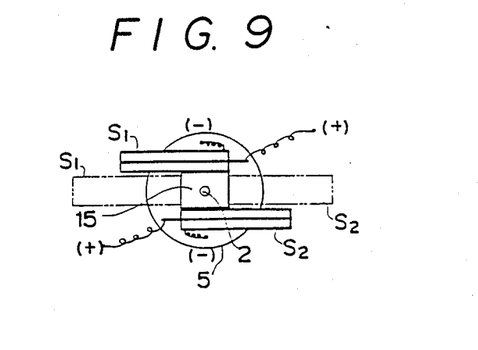
FIG. 9 is a plan view of the vibration sensor.

As shown in FIGS. 8 and 9, a base 15 having a rectangular cross section is attached integrally to the vibration transmission member 2 and the proximal ends of the vibration elements $S_1$ and $S_2$ are attached to the opposite sides of the base 15 so that the flat surfaces of the external electrodes of the vibration elements $S_1$ and $S_2$ are parallel to the opposite sides of the base 15 and so that the free ends of the vibration elements $S_1$ and $S_2$ are directed away from each other, thus establishing the axially symmetrical arrangement of the vibration elements $S_1$ and $S_2$. As shown by the phantom lines in FIG. 9, the vibration elements $S_1$ and $S_2$ may extend along the same straight line in an axially symmetrical manner. In addition, any other attaching means may be used in place of the base 15 insofar as the aforementioned axially symmetrical arrangement of the vibration elements $S_1$ and $S_2$ is obtainable.

The vibration of the detection terminal 3 about the common axis within the liquid 9 is transmitted to the vibration sensor 1B through the transmission member 2, thereby driving the vibration sensor 1B about the common axis to actuate the vibration elements $S_1$ and $S_2$ as described above. As a result, a voltage output corresponding to the vibration of the vibration sensor 1B is produced between the positive and negative voltage terminals. The voltage output thus produced is displayed as a signal indicative of the viscosity or specific gravity of the liquid 9. The detection signal is also used for controlling the vibrator 1A so that the vibrator 1A can vibrate at the resonance frequency of the vibration system at all times. This will be understood from the following description.

Figure 11:
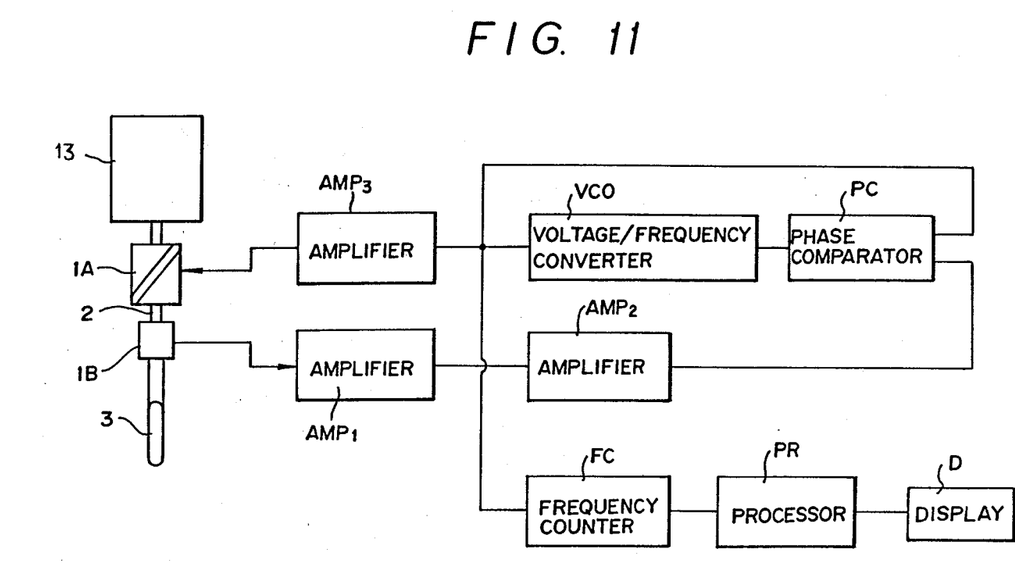
FIG. 11 is a flow chart illustrating a detection and control circuit application to the device when used for detecting the specific gravity of liquid.
Figure 12:
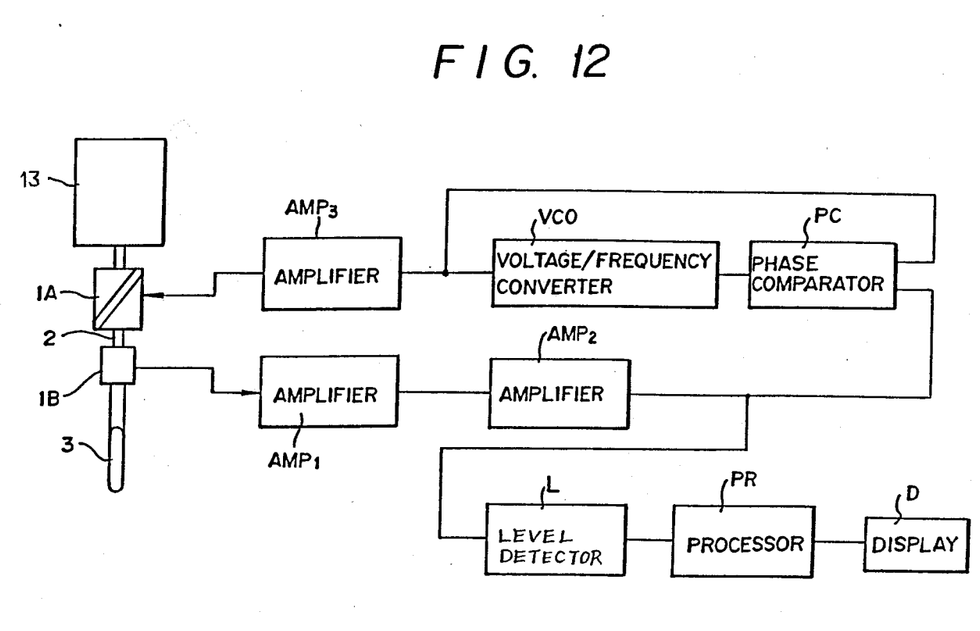
FIG. 12 is a flow chart illustrating a detection and control circuit applicable to the device when used for detecting the viscosity of liquid.

FIG. 11 is a flow chart illustrating a detection and control circuit adopted when the present invention is used for detecting the specific gravity of liquid and FIG. 12 is a flow chart illustrating a detection and control circuit adopted when the present invention is used for detecting the viscosity of liquid. These circuits control the vibrator 1A to be driven at the resonance frequency of the vibration system at all times and, when the resonance frequency is varied due to the immersing of the detection terminal 3 in the liquid 9, also control the vibrator 1A to be driven at the varied resonance frequency. With the circuit shown in FIG. 11, the resonance frequency of the vibrator 1A with the detection terminal 3 placed in air is compared with that of the vibrator 1A with the detection terminal 3 immersed in the liquid 9, the difference in resonance frequency is detected and calculated in terms of a specific gravity value, and the value is displayed. In the circuit shown in FIG. 12, the vibration level (voltage level) of the vibrator 1A with the detection terminal placed in air is compared with that of the vibrator 1A with the detection terminal 3 immersed in the liquid 9, the difference in vibration level is detected and calculated in terms of a viscosity value, and the value is displayed. The frequency of a drive signal is controlled by data corresponding to the phase of each detected signal, thereby controlling the vibrator 1A to be driven at all times at the resonance frequency of the vibration system.

In each of the circuits shown in FIGS. 11 and 12, an electric signal (voltage) proportional to angular acceleration is obtained as a detection signal from the vibration sensor 1B and is issued through amplifiers $AMP_1$ and $AMP_2$ to a phase comparator PC, and an output signal from a voltage/frequency converter VCO is issued through an amplifier $AMP_3$ to the vibrator 1A and is also issued to the phase comparator PC. The phase comparator PC compares the phases of the two signals issued thereto and, when the phase difference is 90 degrees, the voltage/frequency converter VCO outputs an electric signal which is supplied through the amplifier $AMP_3$ to the vibrator 1A for controlling the vibrator 1A to be vibrated at all times at the resonance frequency.

When detecting the specific gravity of the liquid 9, as shown in FIG. 11, the resonance frequency detected by the vibration sensor 1B when the detection terminal 3 has been immersed in the liquid 9 is counted by a frequency counter FC, calculated in terms of specific gravity by a processor PR, and displayed on a display D. When detecting the viscosity of the liquid 9, as shown in FIG. 12, the vibration level (an angular acceleration output signal) detected by the vibration sensor 1B when the detection terminal 3 has been immersed in the liquid 9 is detected by a level detector L, calculated in terms of a viscosity value by a processor PR, and displayed on a display D.

As has been described above, according to the present invention, since the viscosity or specific gravity of liquid can be detected by vibrating a detection terminal with a vibrator and simultaneously detecting the vibration of the detection terminal in the liquid with a vibration sensor provided on a vibration transmission member through which the vibrator and the detection terminal are connected to each other, the unstable operation (due to disturbance of the resonance point) and detection errors (due to the use of a bridge circuit) of the related art using a vibrator both as a drive source and as a vibration sensor can effectively be eliminated.

Furthermore, according to the present invention, since the vibration sensor attached to the vibration transmission member can be positioned as close to the detection terminal as possible, vibration of the detection terminal within the liquid can be precisely detected by the vibration sensor. By using an acceleration sensor as the vibration sensor, even vibration of a very small magnitude can be precisely detected. In addition, use of an angular acceleration sensor as the vibration sensor makes it possible to precisely detect only vibration of the detection terminal about a common axis without being adversely affected by any external vibration.

What is claimed is:

1. A device for detecting the viscosity of specific gravity of a liquid, said device comprising:

a housing;

an inertia mass disposed in said housing, and vibration absorbing means connected between said inertia mass and said housing for supporting said inertia mass within said housing and for absorbing vibration transmitted from said inertia mass toward said housing;

a vibrator comprising piezoelectric ceramics rigidly connected to said inertia mass and having a central axis, said vibrator capable of vibrating about the central axis;

a vibration transmission member having first and second ends, said vibration transmission member connected at said first end thereof to said vibrator;

a detection terminal disposed outside said housing and connected to said vibration transmission member at said second end thereof, said detection terminal vibratable via said vibration transmission member by said vibrator;

resonant frequency establishing means for establishing a desired resonant frequency of said vibrator, said resonant frequency establishing means comprising a mass having a predetermined moment of inertia fitted around said vibration transmission member between said vibrator and said detection terminal; and a vibration sensor disposed on said vibration transmission member for detecting vibration of said detection terminal when said detection terminal is immersed in a liquid and vibrated by said vibrator via said vibration transmission member.

2. A device for detecting the viscosity or specific gravity of a liquid as claimed in claim 1, wherein said vibration sensor issues signals corresponding to the vibration of said detection terminal, and further comprising control means operatively connected to said vibrator and said vibration sensor for receiving said signals and for controlling said vibrator to vibrate at said resonant frequency based on said signals received.

3. The device according to claim 1, wherein said vibration sensor is an acceleration sensor.

4. The device according to claim 1, wherein said vibration sensor is an angular acceleration sensor.

* * * * *